(12) United States Patent
Oster et al.

(10) Patent No.: US 11,975,188 B2
(45) Date of Patent: May 7, 2024

(54) THIN FILM ELECTRODE ASSEMBLY

(71) Applicant: Cirtec Medical Corporation, Brooklyn Park, MN (US)

(72) Inventors: Dan Oster, Brooklyn Park, MN (US); Jeremy Lug, Brooklyn Park, MN (US); Johnny Khith, Brooklyn Park, MN (US); Norbert Kaula, Brooklyn Park, MN (US)

(73) Assignee: Cirtec Medical Corp., Brooklyn Park, MN (US)

( * ) Notice: Subject to any disclaimer, the term of this patent is extended or adjusted under 35 U.S.C. 154(b) by 466 days.

(21) Appl. No.: 17/154,743

(22) Filed: Jan. 21, 2021

(65) Prior Publication Data

US 2021/0220641 A1    Jul. 22, 2021

Related U.S. Application Data

(60) Provisional application No. 63/002,857, filed on Mar. 31, 2020, provisional application No. 62/963,996, filed on Jan. 21, 2020.

(51) Int. Cl.
*A61N 1/05* (2006.01)
*H01B 7/04* (2006.01)

(52) U.S. Cl.
CPC ......... *A61N 1/0558* (2013.01); *A61N 1/0553* (2013.01); *A61N 1/0556* (2013.01); *H01B 7/04* (2013.01)

(58) Field of Classification Search
CPC .. A61N 1/0558; A61N 1/0553; A61N 1/0556; H01B 7/04
See application file for complete search history.

(56) References Cited

U.S. PATENT DOCUMENTS

| | | | |
|---|---|---|---|
| 2007/0027514 A1* | 2/2007 | Gerber | A61N 1/05 607/116 |
| 2008/0046051 A1* | 2/2008 | Skubitz | A61N 1/0553 607/116 |
| 2014/0188202 A1* | 7/2014 | Zarembo | A61N 1/0556 607/118 |
| 2018/0369574 A1* | 12/2018 | Dubuclet | A61N 1/0553 |

* cited by examiner

*Primary Examiner* — Ankit D Tejani
*Assistant Examiner* — Joshua Brendon Solomon
(74) *Attorney, Agent, or Firm* — Haynes and Boone, LLP

(57) ABSTRACT

An apparatus includes an elongate thin film body extending from a first end to a second end. A plurality of electrodes is disposed on the thin film body. A plurality of electrode connection traces each coupled to a respective one of the electrodes. A plurality of attachment structures is placed at predetermined locations about the thin film body. An outer molding surrounds the thin film body. The attachment structures provide connection points for the outer molding, thus allowing for adhesion between the outer molding and the thin film body.

20 Claims, 13 Drawing Sheets

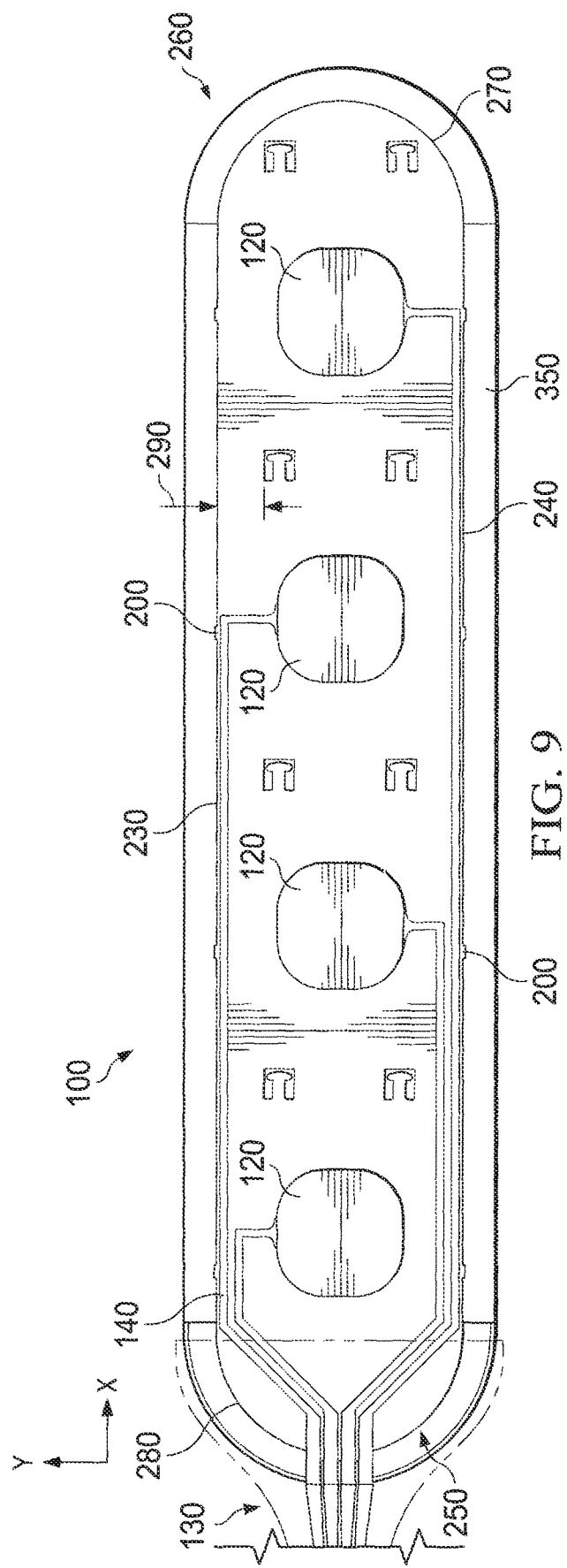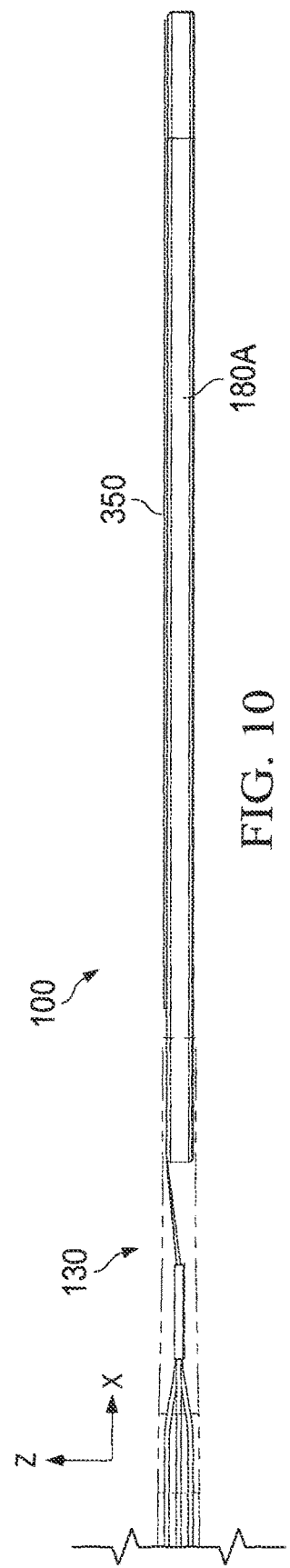

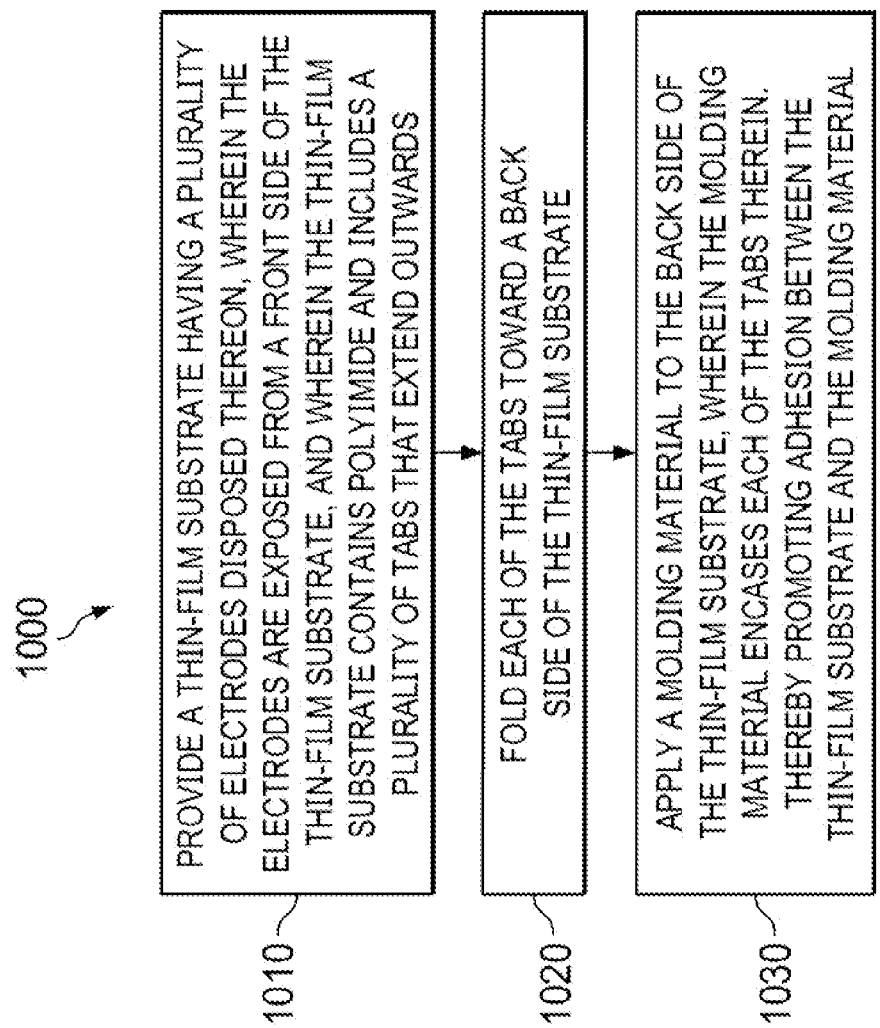

THIN FILM ELECTRODE ASSEMBLY

PRIORITY DATA

The present application is a utility application of U.S. Provisional Application No. 62/963,996, filed on Jan. 21, 2020, entitled "Thin Film Electrode Assembly" and U.S. Provisional Application No. 63/002,857, filed on Mar. 31, 2020, entitled "Connection Mechanism for Thin Film Stimulation Leads", the disclosures of each of which are hereby incorporated by reference in their respective entireties.

BACKGROUND

Electrode assemblies are used in several different medical applications to provide electrical stimulation for the treatment of many different conditions. In use, current electrode assemblies are part of a stimulating system, which also includes a cooperating stimulator to produce electrical pulses that can be delivered to an area of the body. Developing and manufacturing implantable electrode assemblies can be very challenging, since components are often small, fragile and easily damaged. Further, conventional manufacturing methods limit the stimulation contact geometry to effectively stimulate excitable tissue. These situations can lead to higher expense, overly complex products, and electrode assemblies which are not optimum for the desired therapy.

In many applications, it is desirable to produce electrode assemblies which are flexible, but also include the necessary mechanical structures needed to provide the desired electrical stimulation signals. Unfortunately, manufacturing limitations have historically provided challenges, since certain amounts of backing material has been required to support electrodes. As an example, existing paddle leads used for stimulation in the epidural space are typically 1-3 mm thick so that metal electrodes can be appropriately supported and protected. In several circumstances and applications, however, it is desirable to have an electrode assembly which is thin and pliable, thus avoiding compression of the nerves, while also allowing conformance to the anatomy, comfort, and the ability to provide better stimulation therapy.

Thin films are utilized for several applications in many different products. Manufacturing technologies and materials have evolved so that thin films can be used as a substrate for multiple electrical components. Thin film can be effectively manufactured to include many different signal traces and electrical elements which could potentially provide a structure for the above-referenced stimulation therapy. That said, thin film substrates alone, such as a polyimide substrate, do not have the desired mechanical rigidity to be effectively implanted and/or placed for electrical stimulation therapies. Further, polyimide thin film substrates do not easily bond or adhere to other substances, thus making it difficult or challenging to work with as a desirable substrate.

When contemplating thin film leads, a further complication involves the electrical connection of the electrodes used and the wire/cable supplying electrical stimulation pulses. Again, the size of signal transmission paths on the thin film structures and the materials used create challenges and complications.

In contrast, well-known/common electrode leads are often formed on other substrate materials, which provides strength and rigidity as necessary. That said, the size and structure needed to create a useable substrate can be undesirable in certain situations, since it is not flexible or thin enough. In most cases, these electrodes based upon traditional substrates have a height dimension which can be as high as three millimeters, and thus creates challenges when being implanted.

Therefore, although conventional electrode leads and their method of fabrication have generally been adequate, they have not been entirely satisfactory in all aspects.

BRIEF DESCRIPTION OF THE DRAWINGS

FIGS. 8-9 are top views of a thin film lead assembly according to an embodiment of the present disclosure.

FIG. 10 is a side view of a thin film lead assembly according to an embodiment of the present disclosure.

FIG. 16 is a flowchart illustrating a method of fabricating a thin film lead assembly according to an embodiment of the present disclosure.

DESCRIPTION

Figure 1:
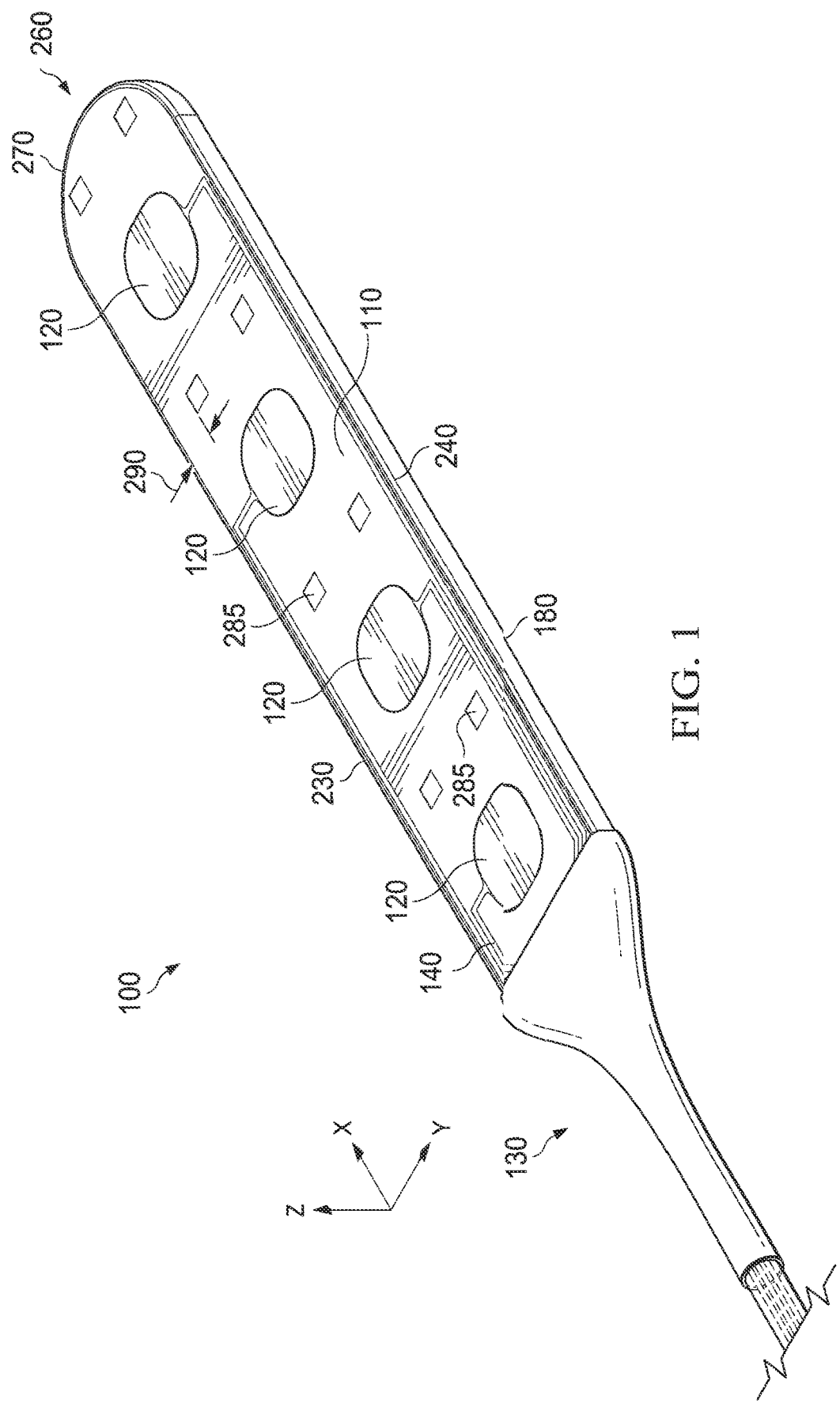
FIGS. 1-2 are three-dimensional perspective views of a thin film lead assembly according to an embodiment of the present disclosure.

Reference will now be made in detail to specific embodiments or features, examples of which are illustrated in the accompanying drawings. Generally, corresponding reference numbers will be used throughout the drawings to refer to the same or corresponding parts. Also, wherever possible, the same reference numbers will be used throughout the drawings to refer to the same or the like parts.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In addition, the present disclosure may repeat reference numerals and/or letters in the various examples. This repetition is for the purpose of simplicity and clarity and does not in itself dictate a relationship between the various embodiments and/or configurations discussed. Moreover, the formation of a feature on, connected to, and/or coupled to another feature in the present disclosure that follows may include embodiments in which the features are formed in direct contact, and may also include embodiments in which additional features may be formed interposing the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 nm" encompasses the dimension range from 4.5 nm to 5.5 nm.

Figure 2:
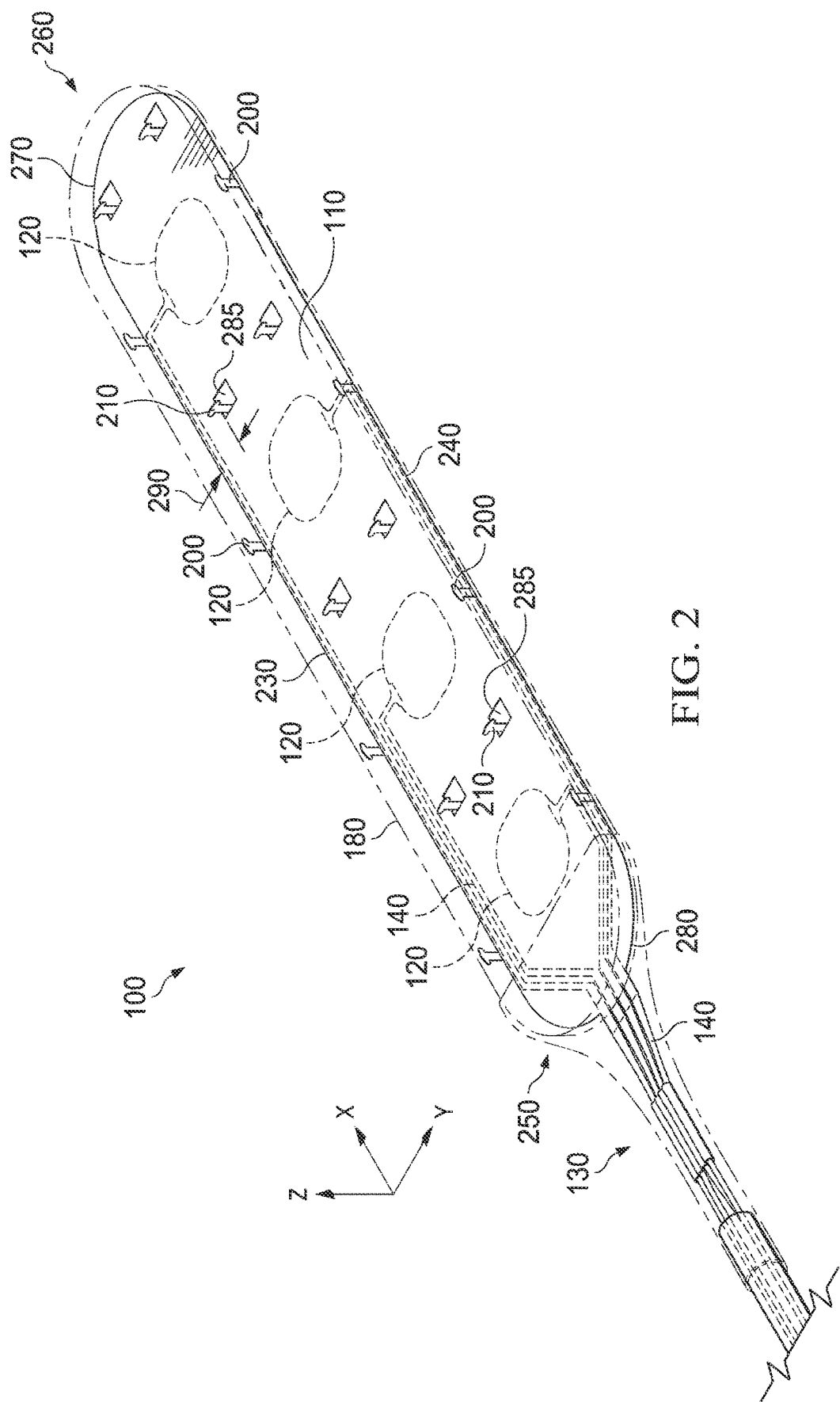
Figure 3:
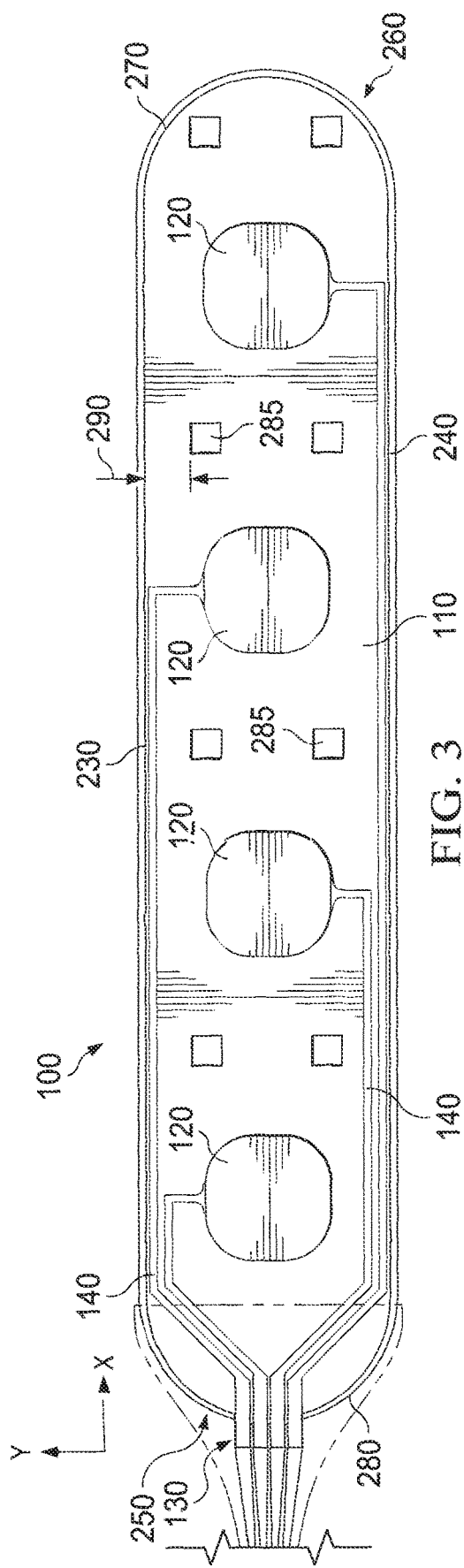
FIG. 3 is a top view of a thin film lead assembly according to an embodiment of the present disclosure.
Figure 4:
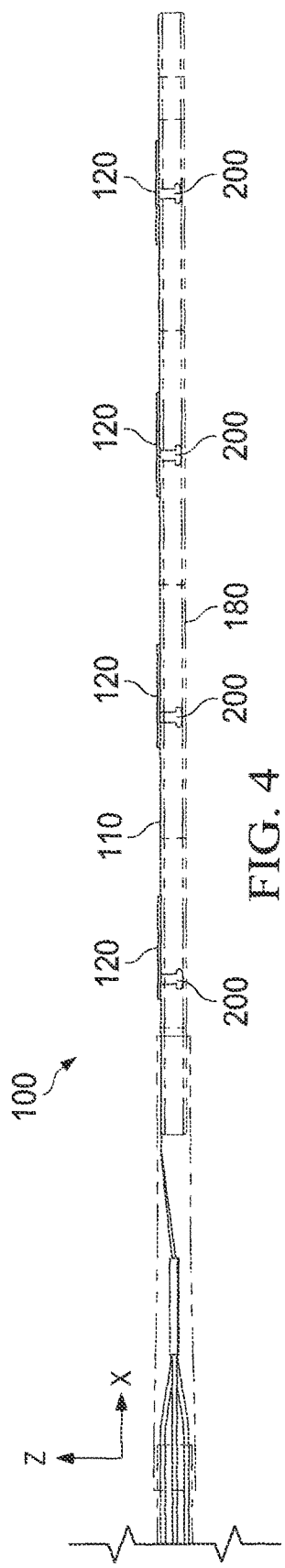
FIG. 4 is a side view of a thin film lead assembly according to an embodiment of the present disclosure.

FIGS. 1-4 illustrate various view of a non-limiting embodiment of a lead assembly 100. In more detail, FIG. 1 illustrates a three-dimensional perspective view of a top side (also interchangeably referred to as a front side) of the lead assembly 100. FIG. 2 illustrates a three-dimensional perspective view of a bottom side (also interchangeably referred to as a back side) of the lead assembly 100. FIG. 3 illustrates a planar view of the top side of the lead assembly 100. FIG. 4 illustrates a side view of the lead assembly 100.

The lead assembly 100 includes a substrate 110 (also referred to as a thin film body) supporting a plurality of electrodes 120, and a related wiring assembly 130. In one embodiment, the wiring assembly 130 is configured to be connected to an electrical stimulator (not shown) or electrical pulse generator. Based on programming instructions received from an electronic programmer (e.g., a clinician programmer or a patient programmer), the electrical stimulator or pulse generator can independently deliver electrical stimulation signals to each of the plurality of electrodes 120. To that end, the wiring assembly 130 and substrate 110 include a plurality of connection traces 140, where each trace 140 is capable of establishing an electrical connection between the electrical stimulator and a corresponding electrode 120. Note that each of the electrodes 120 is positioned on a top side of the thin film substrate 110 and may be flush with the planar surface of the thin film substrate 110, thus allowing for stimulation pulses to be provided to a portion of a patient's body (e.g., spinal cord) when the top side of the lead assembly 100 is appropriately positioned with respect to the patient's body.

Figure 5:
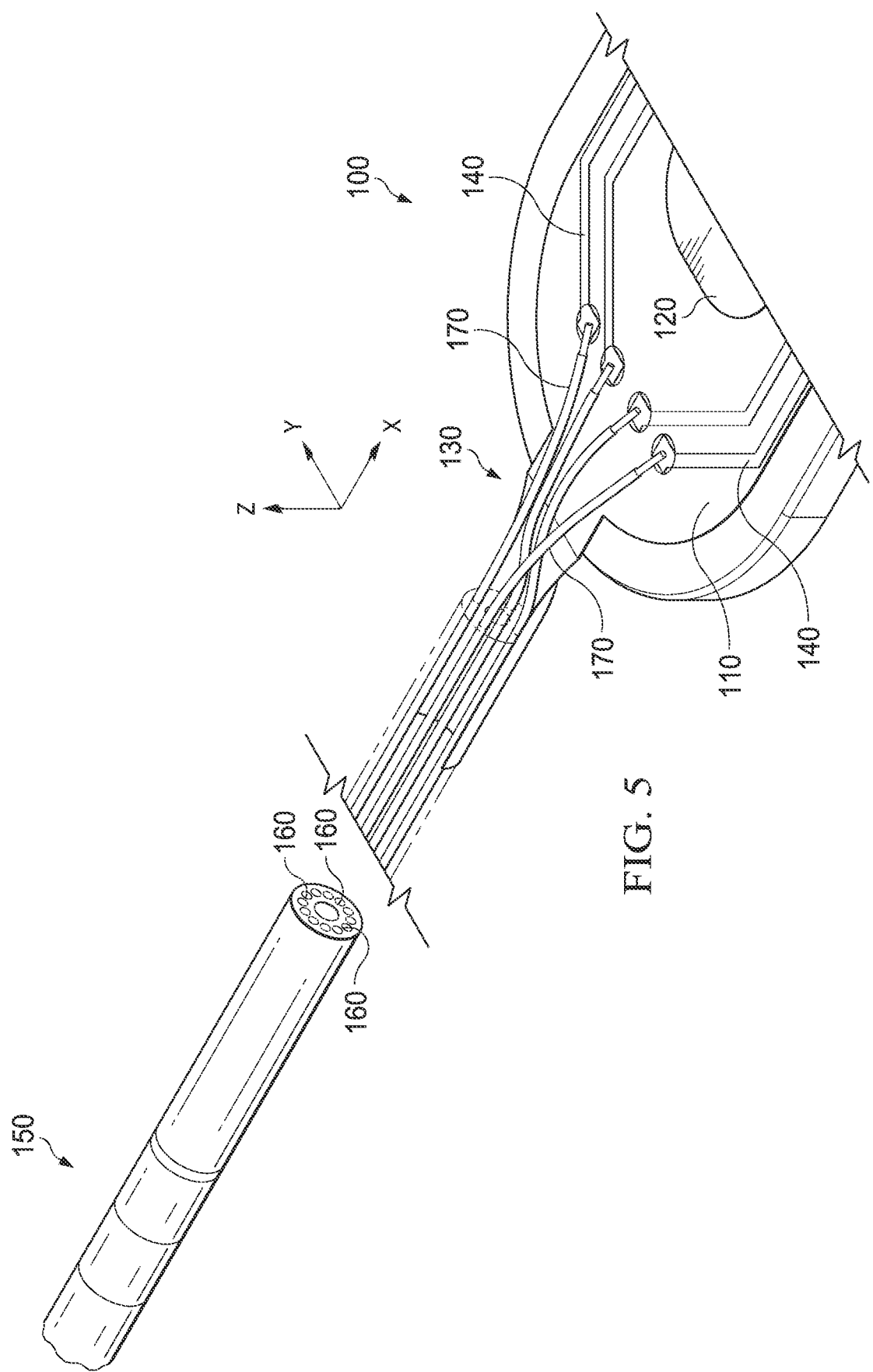
FIG. 5 is a three-dimensional perspective view of multi-lumen lead and a portion of a thin film lead assembly according to an embodiment of the present disclosure.

For example, FIG. 5 illustrates a multi-lumen lead 150 and a portion of the lead assembly 100. As shown in FIG. 5, the connection traces 140 insure the electrical connection to each of the electrodes 120 when coupled with the multi-lumen lead 150. The multi-lumen lead 150 includes an electrically insulating material containing multiple lumens 160, which are separated and isolated from one another, thereby providing an ability to separately energize multiple electrodes 120 simultaneously. In this embodiment, each of the connection traces 140 is individually connected to a respective one of a plurality of connection wires 170 (also referred to as supply wires). The connection wires 170 are then individually inserted or placed within separate lumens 160, thus achieving the necessary electrical connections between the multi-lumen lead 150 and the connection traces 140. Once the connection traces 140 are appropriately electrically connected to the multi-lumen lead 150 (e.g., via the connection wires 170), the lead assembly 100 can be then encapsulated as desired. As such, the connection traces 140 and connection wires 170 provide an effective and efficient mechanism to achieve electrical connection with the multi-lumen lead 150. It is understood that although the connection traces 140 are illustrated as extending in a single plane herein, these could also be staggered, stacked or designed in alternative arrangements, thereby helping to control the profile of the connection traces and potentially reduce overall size of these structures.

Referring back to FIGS. 1-4, the substrate 110 is a polyimide thin film substrate, but those skilled in the art will recognize that several alternative materials could also be used. As will also be appreciated by those skilled in the art, polyimide substrates are well understood and generally provide efficient mechanisms to support electrical components. Multilayer structures, such as the polyimide substrate structure, can be easily achieved through existing or known manufacturing processes, thus creating a desired substrate specifically configured to address specific needs. In some embodiments, the thin film substrate 110 may be formed by forming a base polyimide on a glass plate, and forming a target metal layer over the base polyimide. Patternable layers, such as photoresist layers, may be formed over the target metal layer and/over the base polyimide. A plurality of photolithography processes (e.g., including processes such as photoresist exposing, etching, developing, photoresist removal, etc.) are then performed to define the shapes and contours of various components on the polyimide (such as the attachment structures of the present disclosure discussed below in more detail), as well as the connection traces 140 by patterning the target metal layer.

That said, although polyimide substrates offer flexibility due to their extremely thinness (e.g., ranging from several microns to tens of microns, which is thinner than a typical human hair), they are also very fragile, thus creating various challenges in real world fabrication and/or usage. For example, one of the challenges is that polyimide does not easily bond to other materials, such as molding materials. This creates additional manufacturing challenges when trying to incorporate these substrates into other devices. Based upon these challenges, polyimide substrates have not been widely incorporated into various products, including stimulation leads/stimulation electrodes.

The present disclosure overcomes these problems discussed above by implementing anchoring mechanisms as a part of the assembly 100, so that the anchoring mechanisms can provide additional adhesion between the thin film substrate 110 and the molding materials. In more detail, the present disclosure forms stimulation leads at least in part by encasing, over molding, or coating portions of the lead itself (e.g., such as the thin film substrate 110) in a silicone material 180. For example, as a part of an overmolded assembly process, the lead assembly 100 is placed into a mold. Silicone or another type of suitable molding material is then injected into the mold, such that the bottom planar surface of the thin film substrate 110 is attached to the silicone when the silicone is hardened. Advantageously, even though the thin film substrate 110 may lack the mechanical strength or rigidity for implantation in a patient's body, the silicone material may provide the needed mechanical strength or rigidity, thus providing a stable and well-accepted structure that can be used for implantation and electrical stimulation therapy. Alternatively, another thermoplastic or thermoset could be used to encase over mold or coat the lead. In one embodiment, the silicone 180 is used primarily as a topcoat, which is attached to the back side, but not the front side, of the thin film substrate 110. Since the stimulation therapy is delivered by electrodes 120 on the front side of the thin film substrate 110, the application of the silicone on the back side does not adversely affect the operation and effectiveness of the stimulation electrodes 120, even though the silicone provides additional structure to the lead assembly 100.

Unfortunately, as mentioned above, the polyimide material in the thin film substrate 110 does not easily adhere to the silicone 180, and vice versa. Even when bonding between the thin film substrate 110 and the silicone 180 is achieved initially, the thin film substrate 110 may peel off from the silicone 180 over time. Such a delamination between the thin film substrate 110 and the silicone 180 may degrade the performance of the lead assembly 100, interfere with the intended operation of the lead assembly, and/or render the lead assembly 100 partially or wholly defective.

To overcome the delamination issue discussed above, the present disclosure implements a plurality of attachment structures, such as attachment structures 200 and attachment structures 210, as specific adhesion structures that are integrated into the thin film substrate 110. In other words, the attachment structures 200 and 210 have the same material composition (e.g., polyimide) as the thin film substrate 110 itself, and they are fabricated alongside the thin film substrate 110 using the same fabrication processes, for example via the same lithography processes that were used to define the shapes and contours of the thin film substrate 110. Or stated differently, the attachment structures 200 and 210 may be viewed as an integral part of the thin film substrate 110 itself, but their unique shapes and locations allow them to be bent in a direction away from the rest of the thin film substrate 110 and into or toward the silicone 180, so as to increase the adhesion between the thin film substrate 110 and the silicone 180, as will be discussed in more detail below.

In the embodiment illustrated in FIGS. 1-4, eight attachment structures 200 and eight attachment structures 210 are implemented at predetermined locations on the substrate 110, though only some of them are specifically labeled herein for reasons of simplicity. The attachment structures 200 may be referred to as "edge tabs", since they are each located on an edge 230 or on an edge 240 of the thin film substrate 110. In that regard, the thin film substrate 110 extends in an elongated manner in an X-direction from a first end 250 to a second end 260, where the electrodes 120 are separated from one another in the X-direction. The planar view of FIG. 3 is defined by the X-direction and a Y-direction that is perpendicular to the X-direction, the side view of FIG. 4 is defined by the X-direction and a Z-direction that is orthogonal to the plane defined by the X-direction and the Y-direction. The three-dimensional perspective views of FIGS. 1-2 illustrate all three of the directions in the X, Y, and Z axis.

As shown in FIGS. 1-3, the planar surface of the thin film substrate 110 has straight edges 230 and 240, which each extend in the X-direction and are spaced apart from one another in the Y-direction. The straight edges 230 and 240 are joined together by rounded edges 270 and 280, which partially extend in both the X-direction and the Y-direction. In the illustrated embodiment, the attachment structure 200 are implemented on the straight edges 230 and 240, but it is understood that they may also be implemented on the rounded edges 270 and 280 in other embodiments.

In comparison to the attachment structures 200, the attachment structures 210 (shown in FIG. 2) are each located in an internal region of the planar surface of the thin film substrate 110, away from the edges 230/240/270/280. Furthermore, the attachment structures 210 have been "lifted" down from the planar surface of the thin film substrate 110 toward the back side (as will be discussed in more detail below), which will leave a window 285 or a cutout 285 in the planar surface for each respective attachment structure 210. As such, the attachment structures 210 may also be referred to as "internal tabs" or "internal cutout tabs." For example, each of the attachment structures 210 may be spaced apart from the nearest edge (e.g., the straight edge 230) by a respective distance 290. In the illustrated embodiment, the distance 290 is measured in the Y-direction. Since the distance 290 directly determines the location of each attachment structure 210 on the thin film substrate 110, the value of the 290 may be configured such that the attachment structures 210 are distributed relatively uniformly throughout the planar surface of the thin film substrate 110. The relatively uniform distribution of the locations of the attachment structures 210 leads to a relatively uniform distribution of the adhesion forces between the attachment structures 210 and the silicone 180.

Figure 6A:
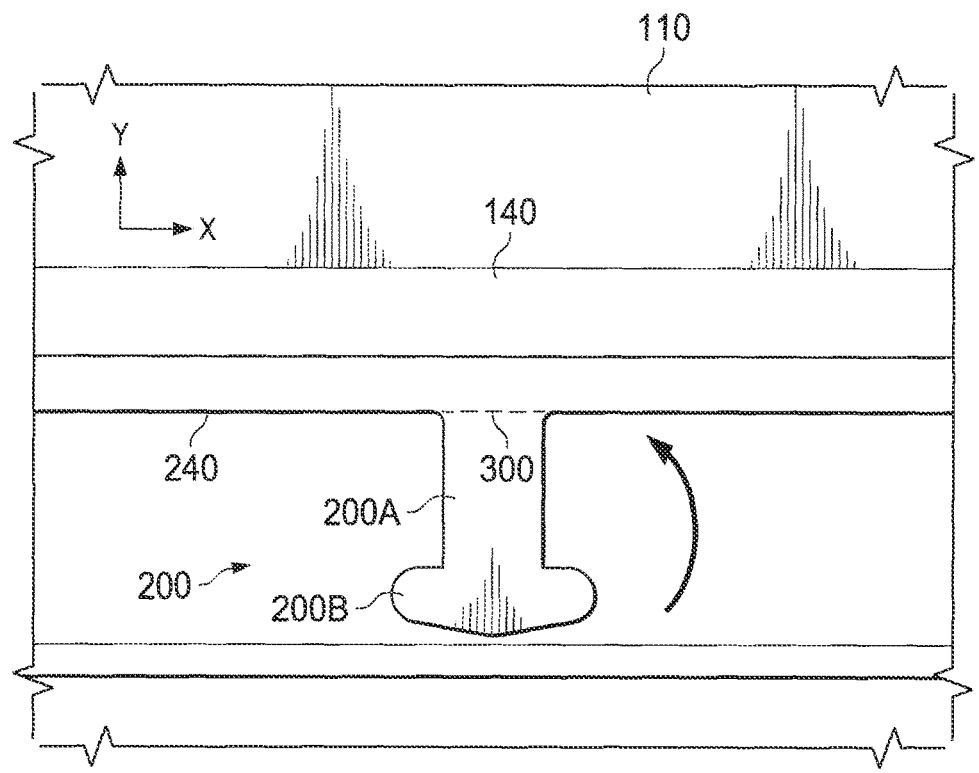
FIGS. 6A-6B each illustrates a magnified top view of attachment structures of a thin film lead assembly according to an embodiment of the present disclosure.
Figure 6B:
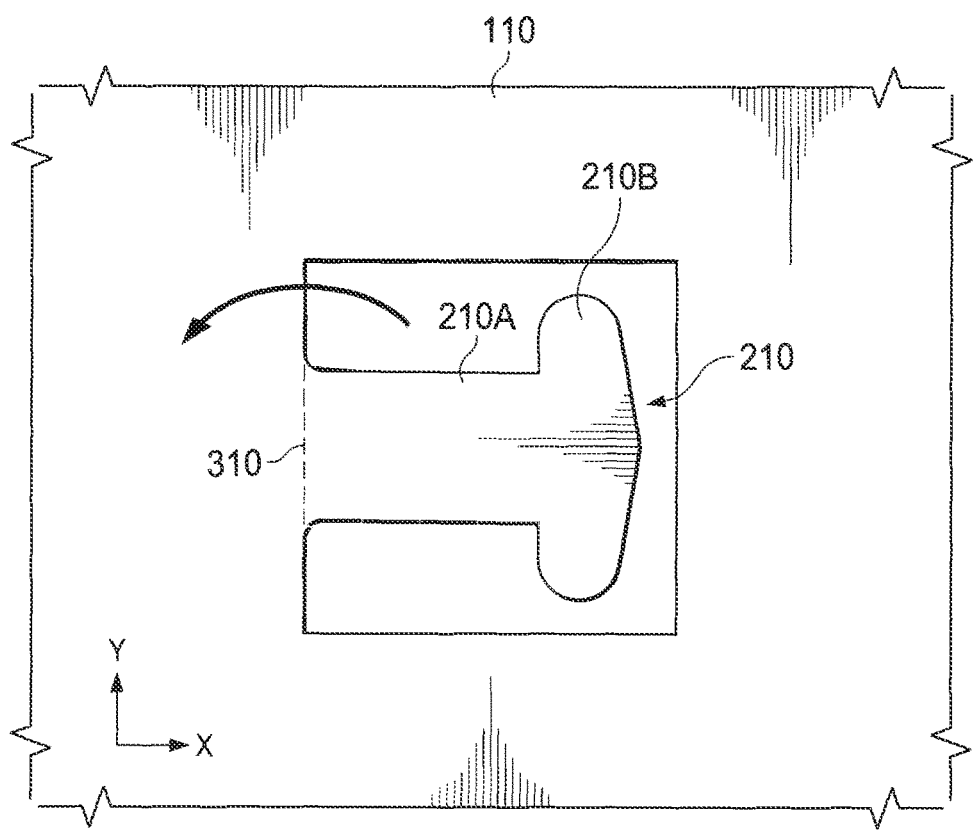

To facilitate the discussion of the attachment structures 200 and 210, FIGS. 6A and 6B illustrate magnified planar views of the attachment structure 200 and the attachment structure 210 (also referred to as adhesion structures), respectively. With reference to FIGS. 1-4 and 6A-6B, the attachment structures 200 and 210 each have a "T-bar" like shape. In other words, the planar view profile or contour of the attachment structures 200 and 210 resemble the capitalized letter "T". For example, the attachment structure 200 includes a body portion 200A and a head portion 200B. The body portion 200A is connected to the edge 240 (or edge 230) of the thin film substrate 110 and extends away from the edge 240 in the Y-direction. The head portion 200B is connected to the body portion 200A and extends in the X-direction. In other words, a dimension of the head portion 200B in the X-direction is substantially greater than a dimension of the head portion 200B in the Y-direction, and the dimension of the head portion 200B in the X-direction is also substantially greater than a dimension of the body portion 200A in the X-direction. Since the attachment structures 200 are located at the edges 230 and 240 of the thin film substrate 110, they may also be referred to as "edge tabs."

Similarly, the attachment structure 210 includes a body portion 210A and a head portion 210B. The body portion 210A is connected to the planar surface of the thin film substrate 110 (or may be reviewed as a part of the planar surface if the thin film substrate 110) and extends in the X-direction. The head portion 210B is connected to the body portion 210A and extends in the Y-direction. In other words, a dimension of the head portion 210B in the Y-direction is substantially greater than a dimension of the head portion 210B in the X-direction, and the dimension of the head portion 210B in the Y-direction is also substantially greater than a dimension of the body portion 210A in the Y-direction.

The attachment structures 200 and 210 are foldable or bendable prior to being encased in the silicone 180, so that they can protrude at an angle away from the planar surface of the thin film substrate 110 before being encased in the silicone 180. For example, the attachment structure 200 is foldable or bendable in the Y-direction and the Z-direction with respect to an imaginary axis 300 (illustrated in FIG. 6A as dashed lines). That is, the attachment structure 200 can be folded or bent along the imaginary axis 300, such that it protrudes away from the planar surface of the thin film substrate 110 at an angle, where the angle is defined by the Z-direction and the planar surface of the thin film substrate 110. In some embodiments, the angle may be substantially 90 degrees. In other words, the attachment structure 200, after being bent or folded, is "coming straight out of the paper" in FIG. 6A. Similarly, the attachment structure 210 may be folded or bent in the X-direction and the Z-direction along an imaginary axis 310, such that it is "coming straight out of the paper" in FIG. 6B.

The attachment structures 200 and 210 promote adhesion with the silicone 180. In more detail, before the thin film substrate 110 is placed into a mold as part of the overmolded assembly process, the attachment structures 200 and 210 are folded or bent to protrude away from the planar surface of the thin film substrate 110 toward the bottom side (e.g., 90 degrees away from the planar surface and toward the bottom side). Thereafter, the lead assembly 100 (with the bent/folded attachment structures) is placed into a mold, and silicone 180 is injected into the mold. When silicone 180 is hardened, the protruded attachment structures 200 and 210 will be encased in (or surrounded by) the silicone 180 from the bottom side of the thin film substrate 110. In this manner, the adhesion between the silicone 180 and the thin film substrate 110 comes not just from a two-dimensional contact area between the planar back surface of the thin film substrate 110 and the silicone 180, but also from the enclosure of the raised (e.g., in the Z-direction) attachment structures 200 and 210 within the silicone 180. Stated alternatively, the bending of the attachment structures 200 and 210 provides a three-dimensional physical connection between the thin film substrate 110 and the encasing material such as the silicone 180. Each attachment structure 200 and 210 provides a separate connection point for the silicone 180 (or another suitable type of outer molding material), thus allowing for enhanced adhesion between the silicone 180 and the thin film substrate 110 and reducing the likelihood of delamination.

The fact that the head portions 200B and 210B are wider (in the X-direction and Y-direction, respectively) than their respective body portions 200A and 210A may further prevent delamination of the silicone 180 from the thin film substrate 110, since such a delamination would pull the attachment structures 200 and 210 away from the thin film substrate 110, but the wider head portions 200B and 210B would resist such a pulling force (i.e., the delamination force) more effectively, thereby making the adhesion between the thin film substrate 110 and the silicone 180 stronger and their delamination even less likely to occur.

In addition, the fact that the attachment structures 200 and 210 are oriented in different directions (e.g., the head portion 200B of the attachment structure 200 extending in the X-direction VS the head portion 210B of the attachment structure 210 extending in the Y-direction) means that the attachment structures 200 and 210 resist being pulled in both the X-direction and the Y-direction, which further increases the amount of force required to delaminate the thin film substrate 110 from the silicone 180. Consequently, the design of orienting the attachment structures 200 and 210 in different (e.g., perpendicular) directions enhances the adhesion between the thin film substrate 110 and the silicone 180.

Furthermore, in embodiments when the attachment structures 210 (i.e., the internal "cutout tabs") are implemented, the silicone (or thermoplastic or thermoset) will fill the "cutout" areas or windows 285 that are formed as a result of the attachment structures 210 being lifted. The presence of the silicone 180 filling these cutout areas or windows 285 creates additional holding structures, which again helps to capture the thin film substrate 110 or promote its adhesion with the silicone 180.

Based on the above discussions, it can be seen that by utilizing specifically designed physical structures such as the attachment structures 200 and/or attachment structures 210, the present disclosure can implement a thin film substrate 110 (e.g., a polyimide substrate) to achieve the desired flexibility and thinness associated with the thin film materials, and at the same time, not suffer from the delamination problems that have plagued traditional thin film leads. As such, the lead assembly 100 of the present disclosure can efficiently and effectively deliver stimulation therapy.

It is understood that although the attachment structures 200 and 210 are implemented with a T-shaped profile in the illustrated embodiment, such a profile is not intended to be limiting. Other configurations and/or geometries could also be used to implement the attachment structures 200 and/or 210. For example, the attachment structures 200 and 210 may not necessarily include a head portion that is differently shaped than the body portion, or they may have differently shaped head portions (e.g., wider, narrower, or exhibit different degrees of curvature), or they may even have multiple head portions, depending on design requirements and manufacturing capabilities and considerations.

Figure 7:
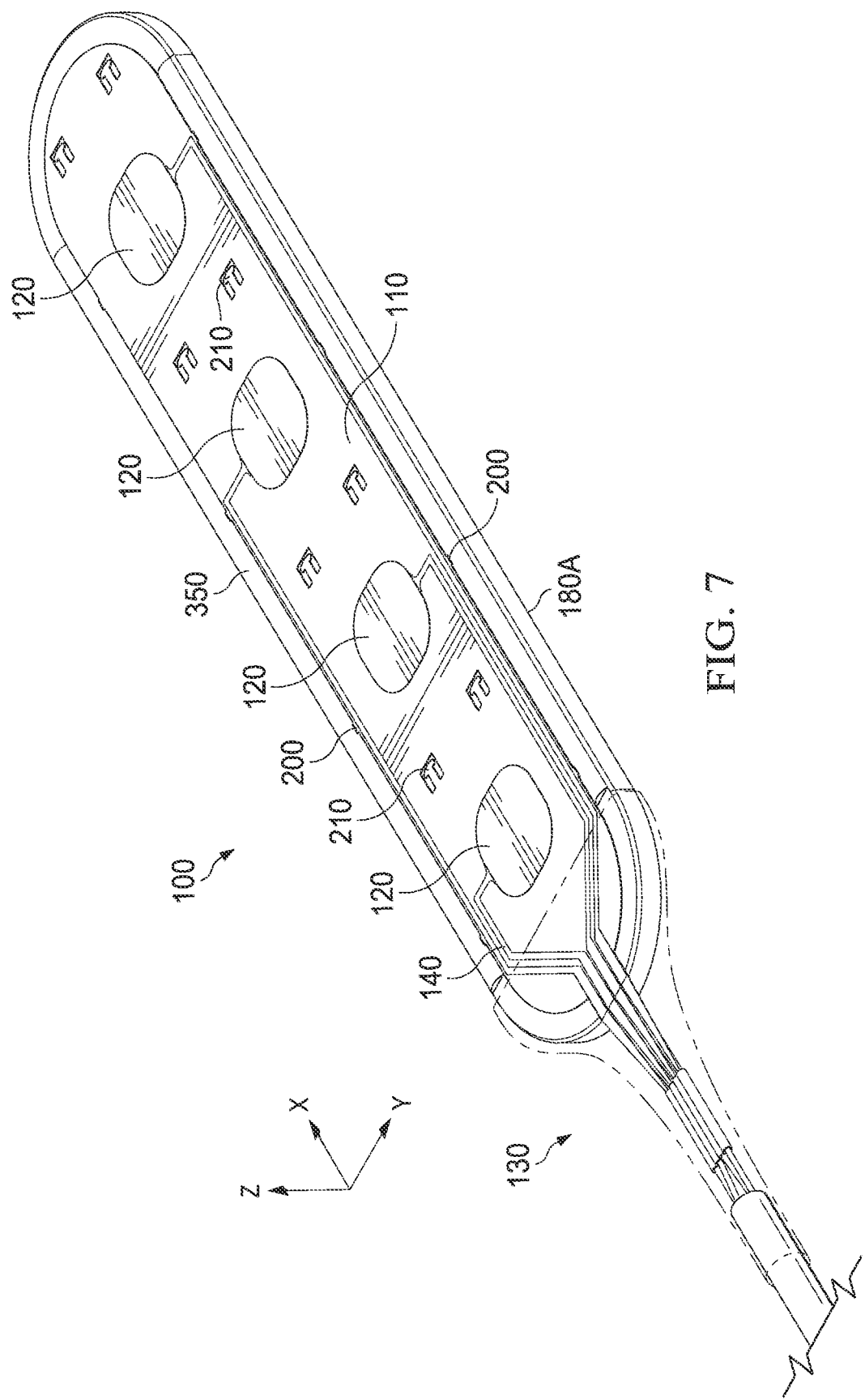
FIG. 7 is a three-dimensional perspective view of a thin film lead assembly according to an embodiment of the present disclosure.
Figure 8:
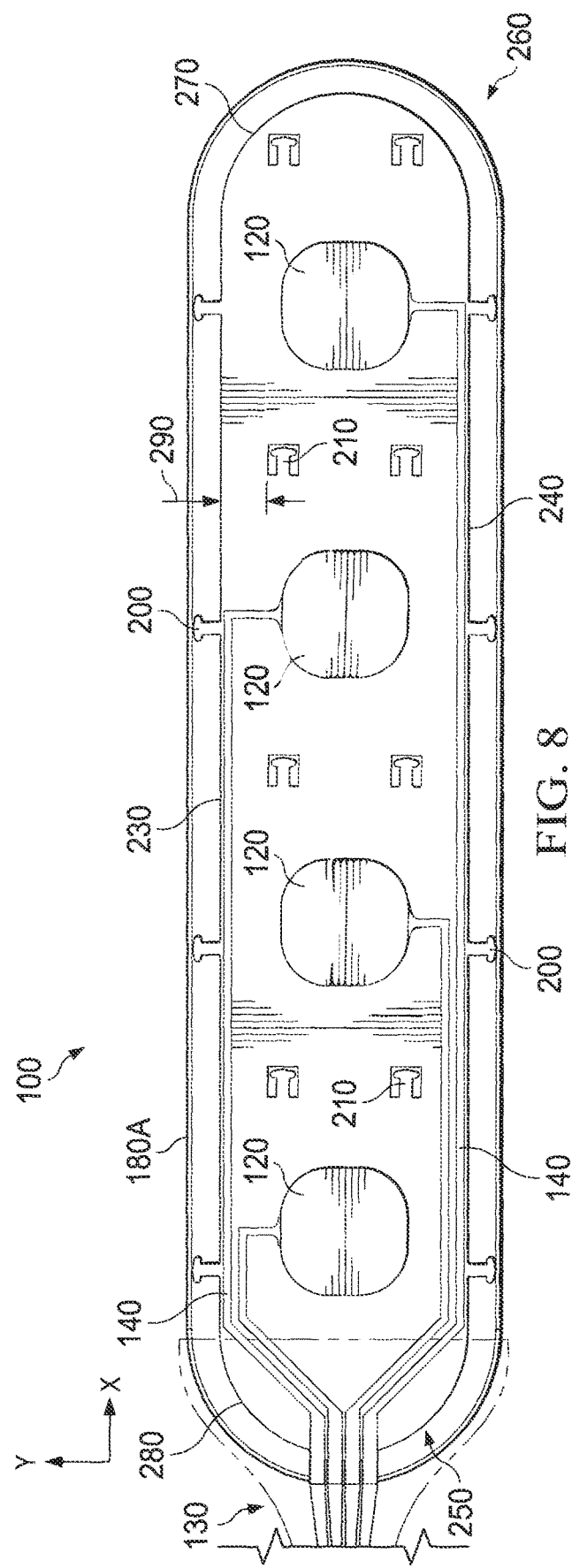

The embodiment discussed above pertains to a paddle lead implementation of the lead assembly 100, where the attachment structures are bent and protrude into the silicone 180 to promote adhesion. FIGS. 7-10 illustrate another embodiment of the lead assembly 100 (still as a paddle lead), where the attachment structures are not bent but rather are coplanar or flush with the rest of the thin film substrate. In more detail, FIG. 7 illustrates a three-dimensional perspective view of a top/front side of the lead assembly 100. FIG. 8 illustrates a planar view of the top/front side of the lead assembly 100 without showing a silicone adhesive. FIG. 9 illustrates a planar view of the top/front side of the lead assembly 100 with the silicone adhesive shown. FIG. 10 illustrates a side view of the lead assembly 100. For reasons of consistency and clarity, similar components appearing in FIGS. 1-10 will be labeled the same.

As shown in FIGS. 7-10, the lead assembly 100 in this embodiment also includes the thin film substrate 110, the electrodes 120, the wiring assembly 130, the conductive traces 140, as well as the attachment structures 200 and 210. However, unlike the embodiment shown in FIGS. 1-4, where the attachment structures 200 and 210 are folded to protrude into the silicone 180 at the bottom side, the attachment structures 200 and 210 are not folded but are rather flush or coplanar with the rest of the thin film substrate 110. For example, as shown clearly in FIG. 8, the attachment structures 200 extend laterally outward from the thin film substrate 110 in the Y-direction. Rather than placing the lead assembly into a mold with the attachment structures 200/210 bent toward the bottom side, the lead assembly 100 in this embodiment is attached to a pre-molded silicone paddle backing 180A. Therefore, the bottom surfaces of the attachment structures 200 and 210 also come into direct physical contact with the pre-molded silicone paddle backing 180A.

To further increase adhesion between the thin film substrate 110 and the pre-molded silicone paddle backing 180A, a thin layer of silicone adhesive 350 is applied over the top surface of the attachment structures 200 after the bottom planar surface of the thin film substrate 110 is attached to the pre-molded silicone paddle backing 180A. As such, both the top surface and the bottom surface of the attachment structures 200 are surrounded by silicone. In other words, the attachment structures 200 protrude laterally (in the Y-direction) into a silicone structure formed by the pre-molded silicone paddle backing 180A and the thin layer of silicone adhesive 350. The majority of the top planar surface of the thin film substrate 110 is still free of having silicone disposed thereon, though some small amounts of the thin layer of silicone adhesive 350 may leak onto the edge regions of the top planar surface of the thin film substrate 110 in some devices. Regardless, the encasement of the laterally-protruding attachment structures 200 in the silicone material still offers sufficient adhesion between the thin film substrate 110 and the pre-molded silicone paddle backing 180A, such that delamination concerns are substantially alleviated.

Note that the attachment structures 210 need not be bent to be encased in the pre-molded silicone paddle backing 180 in this embodiment, which may simplify fabrication of the lead assembly 100. It is also understood that the thin layer of silicone adhesive 350 may or may not have the same material composition as the pre-molded silicone paddle backing 180A. For example, in some embodiments, the pre-molded silicone paddle backing 180A may be configured to have more rigidity than the thin layer of silicone adhesive 350, but the thin layer of silicone adhesive 350 may be configured to be have greater adhesive properties than the pre-molded silicone paddle backing 180A. This is because the pre-molded silicone paddle backing 180A needs to provide form and structure to the lead assembly, whereas the thin layer of silicone adhesive 350 needs to firmly attach itself to the attachment structures 200 (and by extension, the thin film substrate 110) and to the pre-molded silicone paddle backing 180A.

Figure 11:
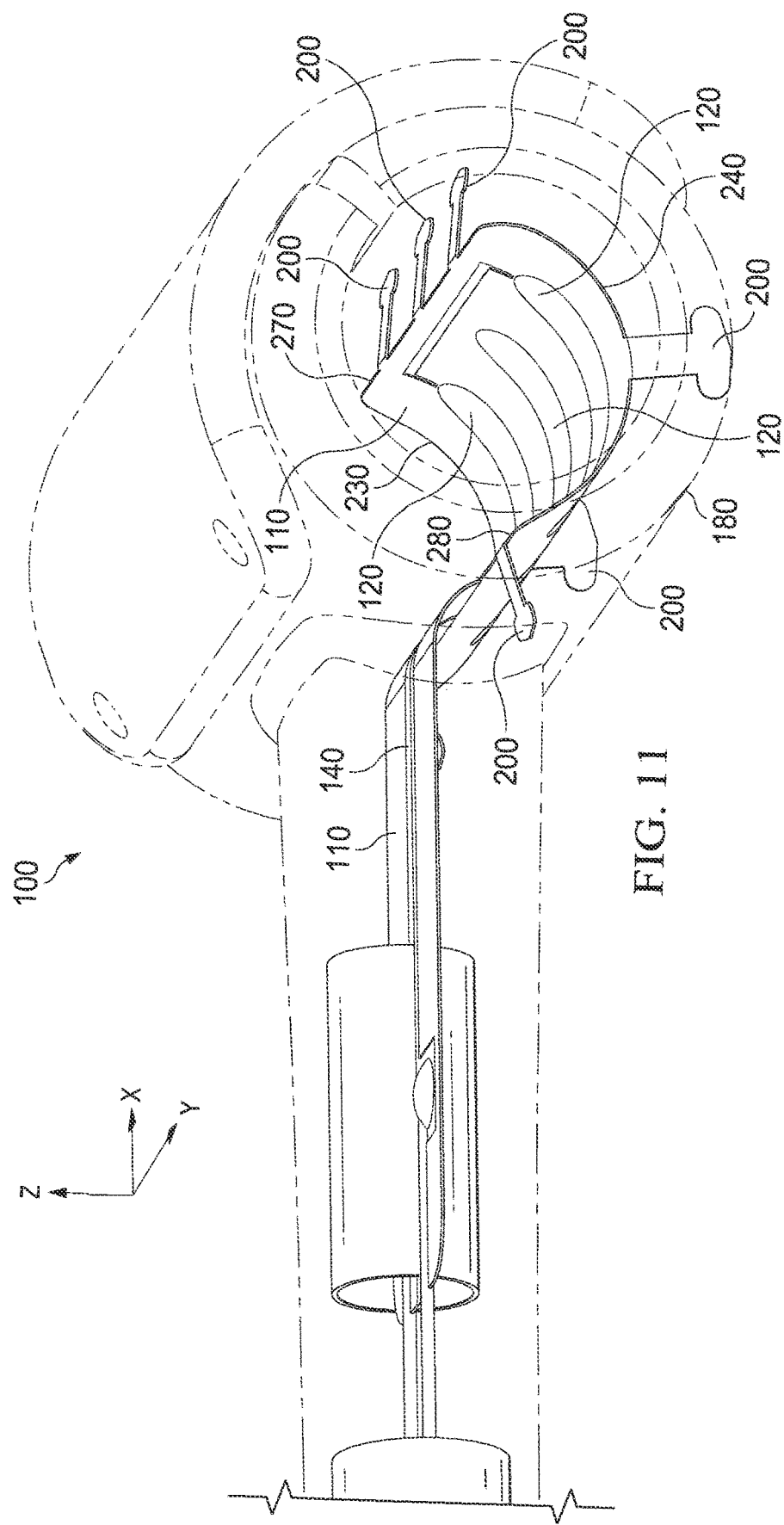
FIGS. 11-12 are three-dimensional perspective views of a thin film lead assembly according to an embodiment of the present disclosure.
Figure 12:
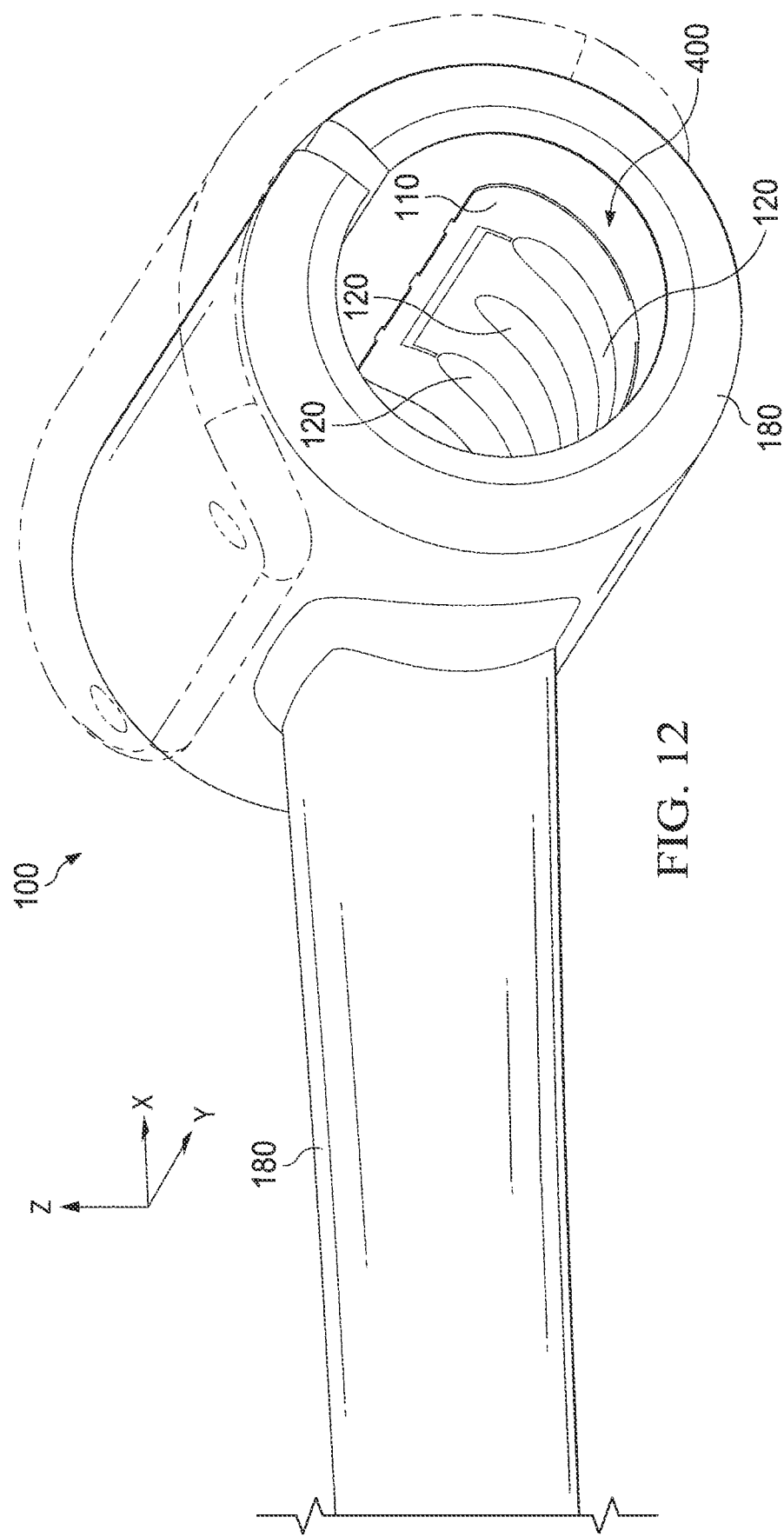
Figure 13:
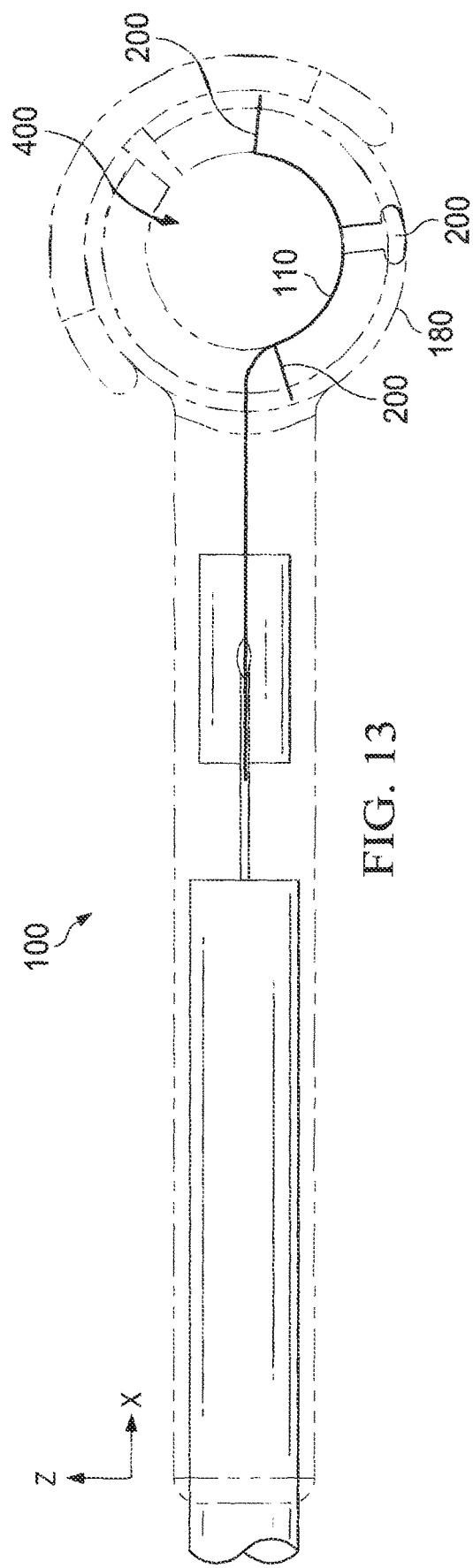
FIGS. 13-14 are side views of a thin film lead assembly according to an embodiment of the present disclosure.
Figure 14:
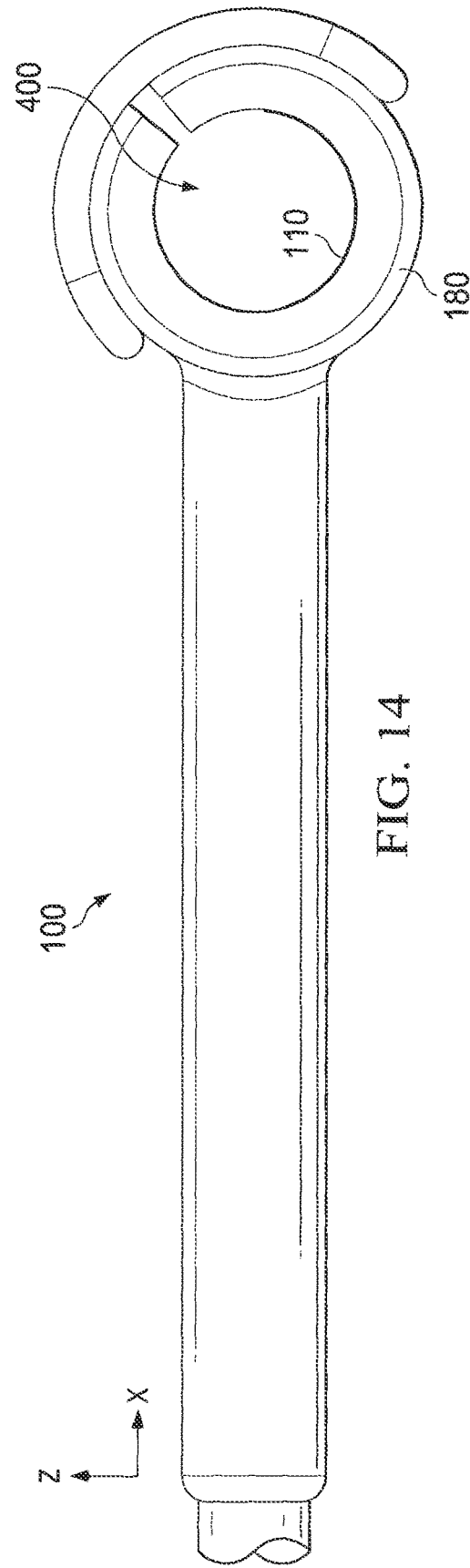
Figure 15:
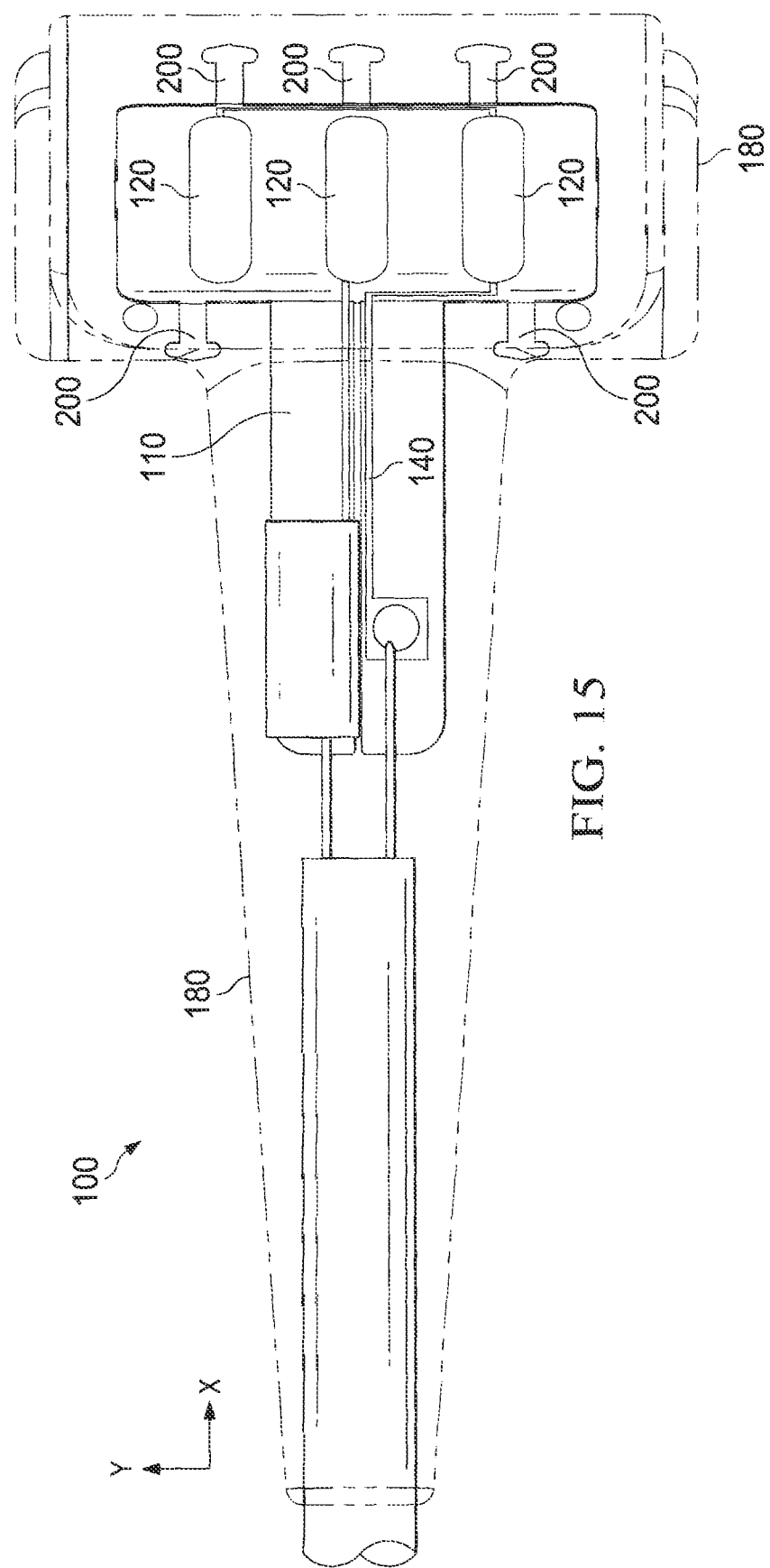
FIG. 15 is a top view of a thin film lead assembly according to an embodiment of the present disclosure.

The two embodiments discussed above each pertains to a paddle lead implementation of the lead assembly 100, one with bent attachment structures, and the other one with unbent attachment structures. FIGS. 11-15 illustrate another embodiment of the lead assembly 100, which is a cuff lead. Specifically, FIG. 11 illustrates a three-dimensional perspective view of the lead assembly 100, where the silicone 180 is illustrated transparently, and where the three dimensions are defined by the X, Y, and Z directions discussed above. FIG. 12 illustrates a three-dimensional perspective view of the lead assembly 100, where the silicone 180 is illustrated non-transparently, and where the three dimensions are also defined by the X, Y, and Z directions discussed above. FIG. 13 illustrates a side view of the lead assembly 100, where the silicone 180 is illustrated transparently. FIG. 14 illustrates a side view of the lead assembly 100, where the silicone 180 is illustrated non-transparently. FIG. 15 illustrates a top view of the lead assembly 100, where the silicone 180 is illustrated transparently. The lead assembly 100 shown in FIGS. 1-4 and 7-10 may hereinafter be interchangeably referred to as a paddle lead assembly, whereas the lead assembly 100 shown in FIGS. 11-15 may be interchangeably referred to as a cuff lead assembly. For reasons of consistency and clarity, similar components appearing in both the paddle lead embodiments and the cuff lead embodiment will be labeled the same.

With reference to FIGS. 11-15, the cuff lead assembly 100 also includes the thin film substrate 110 on which the electrodes 120 are located to deliver electrical stimulation. Unlike the paddle lead assembly 100 (whose thin film substrate 110 has flat planar front and back side surfaces), the thin film substrate 110 of the cuff lead assembly 100 has a curved planar front and back side surfaces. For example, as shown in FIGS. 12-14, the silicone 180 is shaped cylindrically and defines an opening 400. The front side of the planar surface of the thin film substrate 110 is exposed to the opening 400, whereas the back side of the planar surface is covered by the silicone 180. Whereas the flatness of the paddle lead assembly 100 makes it suitable for spinal cord stimulation, the curvature of the cuff lead assembly 100 allows it to be used in peripheral nerve stimulation. For example, a peripheral nerve may run through the opening 400, such that the front side of the electrodes 120 (see FIG. 12) may stimulate the peripheral nerve that is runs through the opening 400.

Similar to the paddle lead assembly discussed above, the electrodes 120 in the cuff lead assembly 100 also have co-planar surfaces with the thin film substrate 110. Stated differently, the exposed surfaces of the electrodes 120 are flush with the planar surface of the thin film substrate at the front side. The back side of the electrodes are also covered up by the silicone 180. As is the case for the paddle lead, the silicone 180 in the cuff lead assembly 100 also does not directly extend to the front side but is located only to the back side of the thin film substrate 110. In other words, no silicone 180 comes into direct physical contact with the front side of the planar surface of the thin film substrate 110. As discussed above, the absence of the silicone 180 at the front side planar surface of the thin film substrate 110 is beneficial, since it reduces the likelihood of the electrodes 120 being pushed away from the target nerve by the "lip" created by what would be the silicone on the front side of the thin film substrate 110. Here, since the front side of the thin film substrate 110 has no silicone 180 (or other types of encasement or molding material) disposed directly thereon, the electrodes 120 can be positioned very close to the target nerves.

The attachment structures 200 of the cuff lead assembly 100 also helps the thin film substrate 110 adhere to the silicone 180, for reasons similar to those discussed above with respect to the paddle lead assembly. In the embodiment shown herein, the attachment structures 200 of the cuff lead assembly 100 also have T-shaped profiles, for example having a wider head portion and a narrower body portion. The attachment structures 200 extend away from the thin film substrate 110 toward the back side, for example at a 90-degree angle with respect to the edge that connects the attachment structure 200 to the thin film substrate 110.

One difference between the paddle lead assembly and the cuff lead assembly is that the cuff lead assembly 100 has one or more attachment structures not only on the edges 230 and 240, but also on the edges 270 and 280 of the thin film substrate 110. The exact number of the attachment structures located on each edge is not intended to be limiting, and other embodiments may implement a different number of attachment structures on each of the edges 230, 240, 270, and 280, and the attachment structures 200 may be located at different locations along the edges 230, 240, 270, and/or 280 than what is shown in the illustrated embodiment herein. Regardless of the number or location of the attachment structures 200, their implementation as an integral component of the cuff lead assembly 100 results in improved adhesion between the thin film substrate 110 and the silicone 180, since the attachment structures 200 reach into, and are surrounded by, the silicone 180 three-dimensionally. As a result, delamination problems plaguing conventional thin film leads are less likely to occur herein.

It is also understood that although the illustrated embodiment of the cuff lead assembly does not have the attachment structures 210 (i.e., the internal "cutout tabs"), that is also not intended to be limiting. In other embodiments of the cuff lead assembly 100, the attachment structures 210 may also be implemented on the thin film substrate 110 at an internal region on the back side, so that these attachment structures 210 will help create further adhesion between the thin film substrate 110 and the silicone 180 by extending into and grabbing onto the silicone 180 located at the back side of the thin film substrate 110.

As generally suggested above, the disclosed design and manufacturing methodology allows for thin film substrates to be utilized as a basis for stimulation leads. The resulting encapsulated assembly is relatively thin and flexible, thus providing a more efficient and effective lead structure. This will generally result in better tissue responses, patient comfort and efficiencies. Example applications for the lead assembly generally discussed above include cortical stimulation and maxillofacial implants. Other options and applications could easily be contemplated, especially given the flexibility and thin profile of the lead assembly.

While the above-mentioned flexibility for the lead assembly 100 provides many advantages, circumstances exist where this same flexibility could provide challenges for implantation or placement. To address this potential complication, one alternative is to add a stylet lumen to the finished/encased electrode assembly which will be configured to provide a desired level of rigidity. Many variations are possible, but one design would provide a stylet lumen that would extend to a distal end of the electrode assembly, thereby providing several desirable features which will aid in the placement and implantation. As a further alternative, stiffening members could be included as part of the assembly. Naturally, such stiffening members could extend partially around the substrate, or could extend in specified locations/positions. Again, several alternatives and configurations for stiffening members could be contemplated and developed. By using stiffening members and/or stylet lumens, the physical characteristics (i.e., flexibility, configuration, pliability, etc.) can be easily modified and controlled to meet many different desired conditions and applications.

FIG. 16 is a flowchart illustrating a method 1000 of fabricating a thin film lead assembly. The method 1000 includes a step 1010 to provide a thin film substrate having a plurality of electrodes disposed thereon. The electrodes are exposed from a front side of the thin film substrate. The thin film substrate contains polyimide and includes a plurality of tabs that extend outwards.

The method 1000 includes a step 1020 to fold each of the tabs toward a back side of the thin film substrate.

The method 1000 includes a step 1030 to apply a molding material to the back side of the thin film substrate. The molding material encases each of the tabs therein, thereby promoting adhesion between the thin film substrate and the molding material.

In some embodiments, the step 1010 comprises fabricating the thin film substrate and the tabs simultaneously at least in part via one or more lithography processes, wherein the tabs are fabricated as integral parts of the thin film substrate.

The devices and methods implemented in the manner described in the present disclosure may offer advantages over conventional devices and methods. However, it is understood that not all advantages are discussed herein, different embodiments may offer different advantages, and that no particular advantage is required for any embodiment.

One advantage is that the attachment structures (e.g., the T-shaped attachment structures 200 and 210 discussed above) may enhance adhesion between the thin film substrate and a molding material such as silicone. Instead of relying on just the adhesion between a planar surface of a thin film substrate and silicone to prevent potential delamination, the attachment structures of the present disclosure offer additional connection points for the silicone material. For example, the attachment structures may extend into the silicone, and their encasement in the silicone makes it more difficult for the thin film substrate to be pulled off of the silicone, or vice versa. As a result, the likelihood of delamination between the thin film substrate and the silicone is substantially reduced. Other advantages include low costs and ease of implementation.

Various embodiments of the invention have been described above for purposes of illustrating the details thereof and to enable one of ordinary skill in the art to make and use the invention. The details and features of the disclosed embodiments are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. An apparatus, comprising:
an elongate thin film body extending from a first end to a second end;
a plurality of electrodes disposed on the thin film body;
a plurality of electrode connection traces that are each coupled to a respective one of the electrodes;
a plurality of attachment structures placed at predetermined locations about the thin film body; and
an outer molding surrounding the thin film body, the attachment structures each terminating into the outer molding, thus allowing for adhesion between the outer molding and the thin film body.

2. The apparatus of claim 1, wherein:
the electrode connection traces are connected with a multi-lumen lead; and
each of the plurality of electrode connection traces and the multi-lumen lead are encased within the outer molding.

3. The apparatus of claim 1, wherein each of the attachment structures include a bendable T-shaped tab that is integrally connected with the thin film body.

4. The apparatus of claim 1, wherein at least a first subset of the attachment structures is located on an edge of the thin film body.

5. The apparatus of claim 4, wherein at least a second subset of the attachment structures are cutout tabs located in an internal area of the thin film body away from the edge of the thin film body.

6. The apparatus of claim 1, wherein the attachment structures each protrude at an angle with respect to a planar surface of the thin film body.

7. The apparatus of claim 1, wherein each of the attachment structures is bendable about an axis prior to being surrounded by the outer molding.

8. The apparatus of claim 1, wherein:
the thin film body includes a polyimide substrate; and
the outer molding includes silicone.

9. The apparatus of claim 1, wherein:
the electrodes are configured to deliver an electrical stimulation therapy from a first side of the thin film body; and the outer molding is disposed on a second side of the thin film body opposite the first side.

10. The apparatus of claim 9, wherein none of the outer molding is disposed directly on the first side of the thin film body.

11. The apparatus of claim 9, wherein a surface of each of the electrodes is flush with a surface of the thin film body at the first side.

12. The apparatus of claim 1, wherein the thin film body is curved.

13. An apparatus, comprising:
a thin film body extending from a first end to a second end;
a plurality of electrodes disposed on the thin film body, wherein the electrodes are configured to deliver electrical stimulation to a nerve issue located adjacent to a first side of the thin film body;
a plurality of electrode connection traces that are each coupled to a respective one of the electrodes, wherein the electrode connection traces are connectable with a multi-lumen lead;
a plurality of attachment structures disposed at different locations of the thin film body; and
an outer molding surrounding the thin film body and the electrode connection traces, wherein the attachment structures each protrude into the outer molding from a second side of the thin film body.

14. The apparatus of claim 13, wherein each of the attachment structures include a bendable tab that is integrally connected with the thin film body, wherein the bendable tab has a T-shaped profile.

15. The apparatus of claim 13, wherein:
at least a first subset of the attachment structures is located on an edge of the thin film body; and
at least a second subset of the attachment structures are cutout tabs located in an internal area of the thin film body away from the edge of the thin film body.

16. The apparatus of claim 13, wherein the attachment structures each protrude at an angle with respect to a planar surface of the thin film body.

17. The apparatus of claim 13, wherein:
each of the attachment structures is bendable about an axis before the attachment structures are protruded into the outer molding;
the thin film body is curved and includes a polyimide material; and
the outer molding includes a silicone material.

18. The apparatus of claim 13, wherein:
no portion of the outer molding is disposed directly on the first side of the thin film body; and
a surface of each of the electrodes is coplanar with a surface of the thin film body at the first side.

19. An apparatus, comprising:
a thin film body extending from a first end to a second end, wherein the thin film body includes a polyimide material;
a plurality of electrodes disposed on the thin film body, wherein the electrodes are configured to deliver an electrical stimulation therapy from a first side of the thin film body;
a plurality of electrode connection traces that are each coupled to a respective one of the electrodes;
a plurality of attachment structures placed at predetermined locations about the thin film body; and
an outer molding disposed on a second side of the thin film body opposite the first side, wherein each of the attachment structures protrude toward and terminate into the outer molding, wherein the outer molding includes a silicone material, and wherein each of the attachment structures is bendable about an axis prior to being surrounded by the outer molding.

20. The apparatus of claim 19, wherein:
each of the attachment structures include a bendable tab that is integrally connected with the thin film body, wherein the bendable tab has a T-shaped profile;
at least a first subset of the attachment structures is located on an edge of the thin film body; and
at least a second subset of the attachment structures are cutout tabs located in an internal area of the thin film body away from the edge of the thin film body.

* * * * *